(12) United States Patent
Hahn et al.

(10) Patent No.: US 11,571,429 B2
(45) Date of Patent: Feb. 7, 2023

(54) METHOD AND COMPOUNDS FOR TREATING PERIPHERAL NEUROPATHY

(71) Applicant: UPEXMED CO. LTD., Anyang-si (KR)

(72) Inventors: Soon Kap Hahn, Irvine, CA (US); Gantumur Battogtokh, Incheon (KR); Oyuntuya Gotov, Incheon (KR); Gil Man Kim, Anyang (KR); Min Hyo Seo, Daejeon (KR)

(*) Notice: Subject to any disclaimer, the term of this patent is extended or adjusted under 35 U.S.C. 154(b) by 28 days.

(21) Appl. No.: 17/135,158

(22) Filed: Dec. 28, 2020

(65) Prior Publication Data

US 2021/0113583 A1 Apr. 22, 2021

Related U.S. Application Data

(63) Continuation-in-part of application No. 15/986,533, filed on May 22, 2018, now abandoned.

(60) Provisional application No. 62/510,240, filed on May 23, 2017.

(51) Int. Cl.

| | | |
|---|---|---|
| *A61K 31/55* | (2006.01) | |
| *A61K 9/16* | (2006.01) | |
| *A61K 31/167* | (2006.01) | |
| *A61K 31/415* | (2006.01) | |
| *A61K 31/135* | (2006.01) | |
| *A61K 9/00* | (2006.01) | |
| *A61K 45/06* | (2006.01) | |
| *A61P 23/02* | (2006.01) | |
| *A61P 25/02* | (2006.01) | |
| *A61K 31/4168* | (2006.01) | |

(52) U.S. Cl.
CPC ............ *A61K 31/55* (2013.01); *A61K 9/0019* (2013.01); *A61K 9/0021* (2013.01); *A61K 9/1647* (2013.01); *A61K 31/135* (2013.01); *A61K 31/167* (2013.01); *A61K 31/415* (2013.01); *A61K 31/4168* (2013.01); *A61K 45/06* (2013.01); *A61P 23/02* (2018.01); *A61P 25/02* (2018.01)

(58) Field of Classification Search
CPC ...... A61P 23/02; A61P 25/02; A61K 31/4168; A61K 45/06; A61K 9/0019; A61K 9/0021; A61K 31/135; A61K 31/415; A61K 31/167; A61K 9/1647; A61K 31/55
See application file for complete search history.

(56) References Cited

U.S. PATENT DOCUMENTS

| | | | |
|---|---|---|---|
| 3,115,441 A | 12/1963 | Hermelin | |
| 2008/0019969 A1* | 1/2008 | Gorman | A61P 37/00 514/401 |
| 2015/0150788 A1* | 6/2015 | Prow | A61K 47/02 424/490 |
| 2016/0136179 A1* | 5/2016 | Criscione | A61K 31/55 514/567 |

FOREIGN PATENT DOCUMENTS

WO    WO-2008021388 A1 * 2/2008 ........... C07D 213/75

\* cited by examiner

*Primary Examiner* — Sean M Basquill
(74) *Attorney, Agent, or Firm* — Cionca IP Law P.C.; Marin Cionca

(57) ABSTRACT

A medicament set adapted to regulate multiple receptors simultaneously in patients experiencing diabetic peripheral neuropathy pain, the medicament set comprising: at least three distinct and separate medicaments for treating diabetic peripheral neuropathy pain, the at least three medicaments being a first medicament for treating peripheral neuropathy pain, being formulated for clinical administration as a locally injectable medicament using an injection device, and comprising polylactic glycolic acid (PLGA) micro-particles being loaded with a sodium channel blocker and local anesthetic drug, a second medicament for treating peripheral neuropathy pain, being formulated for clinical administration as a locally injectable medicament using an injection device, and comprising PLGA micro-particles being loaded with a sodium channel blocker and anti-convulsant drug, and a third medicament for treating peripheral neuropathy pain, being formulated for clinical administration as a locally injectable medicament using an injection device, and comprising PLGA micro-particles being loaded with an anti-inflammatory drug.

4 Claims, 7 Drawing Sheets

METHOD AND COMPOUNDS FOR TREATING PERIPHERAL NEUROPATHY

CROSS-REFERENCE TO RELATED APPLICATIONS

This application is a continuation-in-part of U.S. Non-Provisional application Ser. No. 15/986,533, filed May 22, 2018, which claims the benefit of U.S. Provisional Application No. 62/510,240, filed May 23, 2017, which are hereby incorporated by reference, to the extent that they are not conflicting with the present application.

BACKGROUND OF INVENTION

1. Field of the Invention

The invention relates generally to methods for treating peripheral neuropathy, including diabetic neuropathy, and more specifically, this invention relates to a comprehensive set of pain management medications, such as sodium channel blockers, N-methyl-D-aspartate (NMDA) receptor antagonists, α-2 adrenergic receptor agonists, anti-inflammatory drugs, calcium channel blockers, and other classes of medications or their mixtures.

2. Description of the Related Art

Peripheral neuropathy, which is a result of damage to the peripheral nerves (i.e., the nerves beyond the brain and the spinal cord), often causes weakness, numbness, and pain in general. These symptoms usually affect the hands and the feet, but they can also be felt in other areas of the human body, as an example. In general, as is known, peripheral neuropathy can result in the impairment of sensation, movement, gland, or organ function, depending on which nerves are damaged in particular. As an example, more than 20 million people in the United States currently have some form of peripheral neuropathy, with this estimated figure likely being significantly higher.

In particular, diabetic neuropathy is one of the most common forms of peripheral neuropathy and is a type of nerve damage that can occur from diabetes (type 1 or 2), for example. High blood glucose level due to diabetes can cause damage to the nerve fibers throughout the body, but diabetic neuropathy most often damages nerves in the hands and the feet. This nerve damage causes symptoms such as tingling, numbness, burning and pain. These symptoms are mild for some people, but they can be extremely painful, disabling and/or even fatal for others. The pathology of diabetic neuropathy is still unknown and there is no treatment to cure diabetic neuropathy. Current methods of treatment are aimed at reducing the pain associated with diabetic neuropathy (i.e., symptomatic treatment).

As an example, the symptomatic treatment typically involves the use of antidepressants, anticonvulsants, or opioid or opioid-like medications that are taken orally. Concerns related to potential side effects associated with these oral medications prevent their widespread use in many patients. Most of these medications require systemic effects targeted mainly on the spinal cord and/or the brain (i.e., the central nervous system) to reduce the pain caused by diabetic neuropathy. However, antidepressants and anticonvulsants taken orally possess significant side effects such as insomnia, dizziness, dry mouth, weight gain, headache, and nausea. Moreover, the long-term use of opioids or opioid-like medications may cause addiction. Thus far, there are only three oral medications approved by the FDA for treating diabetic neuropathy: duloxetine ("Cymbalta", antidepressant), pregabalin ("Lyrica", anti-convulsant) and tapentadol ("Nucynta", opioid). However, these medications are known to be suboptimal in reducing pain and related symptoms, with only about 50% effectiveness for diabetic neuropathy patients.

Regarding the experience of pain in the body, numerous mechanisms related to transduction or transmission functions have been linked in causing pain. As is known, these transduction or transmission functions involve multiple receptors. Typically, the above-mentioned oral medications for treating painful diabetic neuropathy function at one specific receptor site. However, each patient may have different mechanism(s) for causing their respective pain. This discrepancy may explain why, for example, antidepressants show a good efficacy for some patients but not for other patients. Since it is difficult to predict specifically in each patient which receptor site to target, the effectiveness outcome of prescribed medications is unpredictable, and therefore less efficient. Alternatively, using multiple oral medications for targeting various receptor sites is not a viable option due to the medications' cumulative side effects and adverse drug-drug interactions.

As another option, local delivery of pain management medications may reduce the pain caused by diabetic neuropathy without the systemic side effects associated with medications delivered orally. In addition, multiple medications can be administered locally to target multiple receptors without causing side effects and adverse drug-drug interactions. Since the plasma concentration of locally delivered medications is only about 5 to 15% (percent) of the corresponding oral medications, the incidence of systemic side effects and adverse drug-drug interactions is dramatically reduced, compared to the systemic use of the same medications delivered orally. There are currently two methods being developed for the local delivery of pain management medications: 1) controlled, sustained delivery by injection of pain medications encapsulated in biodegradable polymer, such as polylactic glycolic acid (PLGA); and 2) passive transdermal delivery of compounded pain management medications.

As an example, the pain management medications can be formulated into a biodegradable polymer such as PLGA, as mentioned above, which degrades over weeks or months. One such approach uses naturally occurring site 1 (one) sodium channel blockers, such as tetrodotoxin (a biological toxin), with other drugs to prolong nerve blocking duration of the biological toxin, and thus improve safety and efficacy. The other drugs include a local anesthetic, vaso-constrictor, glucocorticoid, and/or adrenergic drugs like alpha-1 agonists (phenylephrine), beta-blockers (propranolol), and alpha-2 agonists (clonidine). The main goal of adding these other drugs is to prolong the nerve blocking duration of the biological toxin, for example. Another approach involves the use of an opioid analgesic drug, such as morphine, and an anti-inflammatory drug, such as dexamethasone, to treat inflammation and pain. These drugs were encapsulated in a biodegradable polymer like PLGA to form a depot for a long-term pain-relieving effect. Compounds such as clonidine and GABA can be used to treat inflammation and pain using PLGA microsphere formulations, as another example. Other pain treatment approaches involve the use of corticosteroid (e.g., triamcinolone acetonide (TCA)), anticonvulsant (e.g., carbamazepine), local anesthetics (e.g., lidocaine), bupivacaine, non-steroidal anti-inflammatory drugs, or glucocorticoids, each encapsulated in PLGA microspheres for treating acute, chronic, or post-operative pain, for example.

Another method involves the use of a passive transdermal delivery system of compounded pain management medications in a cream formulation. This method includes a comprehensive set of pain management medications including anti-inflammatory, local anesthetic, calcium channel blocker, gabapentin, tricyclic anti-depressant, baclofen, clonidine, ketamine, and other drugs, for example.

The above-described methods include the use of various pain management medications encapsulated in the PLGA microspheres for treating acute or chronic pains, including neuropathic pains. However, none of these PLGA-based methods include a comprehensive set of pain management medications. The pathology of pain, especially neuropathic pain including diabetic neuropathy, is not well elucidated and may involve multiple receptors, as mentioned previously above. Effective treatment should consider inclusion of a comprehensive set of pain management medications. The passive transdermal delivery of compounded pain management medications may provide delivery of comprehensive pain management medications without causing systemic side effects. However, the passive diffusion of pain management medications across the skin is inconsistent in its delivery amount. In addition, this method requires topical application several times per day, which is cumbersome.

Therefore, there is a need to solve the problems described above by providing compounds and methods for effectively, conveniently, and safely treating peripheral neuropathy, and in particular, diabetic neuropathy.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect, a medicament set adapted to regulate multiple receptors simultaneously in patients experiencing diabetic peripheral neuropathy pain is provided. The medicament set may comprise: at least three distinct and separate medicaments for treating diabetic peripheral neuropathy pain, the at least three medicaments being a first medicament for treating peripheral neuropathy pain, being formulated for clinical administration as a locally injectable medicament using an injection device, and comprising polylactic glycolic acid (PLGA) micro-particles being loaded with a sodium channel blocker and local anesthetic drug, a second medicament for treating peripheral neuropathy pain, being formulated for clinical administration as a locally injectable medicament using an injection device, and comprising PLGA micro-particles being loaded with a sodium channel blocker and anti-convulsant drug, and a third medicament for treating peripheral neuropathy pain, being formulated for clinical administration as a locally injectable medicament using an injection device, and comprising PLGA micro-particles being loaded with an anti-inflammatory drug, wherein the PLGA micro-particles of the first, the second, and the third medicaments have a size between 1 µm and 50 µm; and wherein an administration of at least a portion of the medicament set using an injection device causes a simultaneous regulation of the multiple receptor sites, such that to alleviate the pain being experienced by the patients having diabetic peripheral neuropathy. Thus, an advantage is that the user-friendly injection method may enable injecting a small amount of pain management medications at multiple sites, which may thus enhance the efficacy of treatment. Another advantage is an advantage is that neuropathic pain may effectively and efficiently be treated in a timely manner. An additional advantage is that neuropathic pain can be effectively treated without the experience of significant adverse side effects.

In another aspect, a method of treating pain caused by diabetic peripheral neuropathy using a medicament set for regulation of multiple receptors simultaneously in a patient experiencing the pain is provided. The method may comprise the steps of: receiving the medicament set, the medicament set comprising at least three distinct and separate medicaments for treating diabetic peripheral neuropathy pain, the three medicaments being a first medicament for treating peripheral neuropathy pain, being formulated for clinical administration as a locally injectable medicament using an injection device, and comprising polylactic glycolic acid (PLGA) micro-particles being loaded with a sodium channel blocker and local anesthetic drug, a second medicament for treating peripheral neuropathy pain, being formulated for clinical administration as a locally injectable medicament using an injection device, and comprising PLGA micro-particles being loaded with a sodium channel blocker and anti-convulsant drug, and a third medicament for treating peripheral neuropathy pain, being formulated for clinical administration as a locally injectable medicament using an injection device, and comprising PLGA micro-particles being loaded with an anti-inflammatory drug, wherein the PLGA micro-particles of the first, the second, and the third medicaments have a size between 1 µm and 50 µm; selecting all or a portion of the medicament set for clinical administration to the patient according to particular information known about the patient, including information about the receptors that need to be simultaneously regulated in the patient to alleviate pain; loading the selected all or portion of the medicament set into an injection device; and administering the selected all or portion of the medicament set to the patient by local injection using the injection device, the administering of the selected all or portion of the medicament set causing a simultaneous regulation of the multiple receptor sites, and thus resulting in at least a partial alleviation of the pain being experienced by the patient having diabetic peripheral neuropathy. Thus, an advantage is that the microparticles of the present invention can be prepared using known, readily available techniques, which may reduce complex design requirements and thus lower manufacturing costs. Another advantage is that the user-friendly injection method may enable injecting a small amount of pain management medications at multiple sites, which may thus enhance the efficacy of treatment. An additional advantage is that neuropathic pain may effectively and efficiently be treated in a timely manner. Another advantage is that neuropathic pain can be effectively treated without the experience of significant adverse side effects.

In another aspect, a method of treating pain caused by diabetic peripheral neuropathy is provided. The method may comprise providing a medicament set adapted to regulate multiple receptors simultaneously in patients experiencing diabetic peripheral neuropathy pain by performing the following steps: selecting at least three distinct and separate drugs for formulating the medicament set comprising at least three distinct and separate medicaments for treating peripheral neuropathy pain, the at least three drugs being a sodium channel blocker and local anesthetic drug, a sodium channel blocker and anti-convulsant drug, and an anti-inflammatory drug; formulating the at least three medicaments by encapsulating each of the at least three drugs individually in polylactic glycolic acid (PLGA) micro-particles having a size between 1 μm and 50 μm, the at least three medicaments each being formulated for clinical administration as a locally injectable medicament using an injection device; and providing instructions to prescribe all or a portion of the medicament set for a particular peripheral neuropathy patient according to particular information known by a doctor about the patient, including information about the receptors that need to be simultaneously regulated in the patient to alleviate pain; wherein an administration of the medicament set using the microneedle injection device causes a simultaneous regulation of the multiple receptor sites, such that to alleviate the pain being experienced by the patient having diabetic peripheral neuropathy. Thus, an advantage is that the microparticles of the present invention can be prepared using known, readily available techniques, which may reduce complex design requirements and thus lower manufacturing costs. Another advantage of the disclosed method is that neuropathic pain may effectively and efficiently be treated in a timely manner. An additional advantage of the disclosed method of treatment is that neuropathic pain can be effectively treated without the experience of significant adverse side effects.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which.

DETAILED DESCRIPTION

Figure 1:
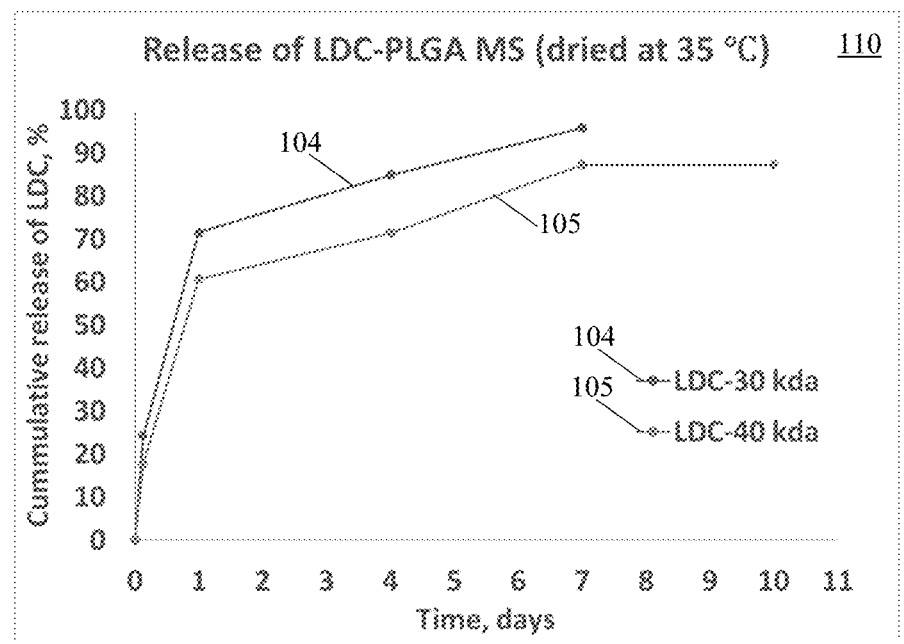
FIG. 1 is a plot illustrating the release profile of a lidocaine-loaded PLGA microsphere (LDC-30 kda and LDC-40 kda), according to an aspect.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the drawings and of the specification, some or all details about some structural components or steps that are known in the art are not shown or described if they are not necessary for the invention to be understood by one of ordinary skills in the art.

For the following description, it can be assumed that most correspondingly labeled elements across the figures possess the same characteristics and are subject to the same structure and function. If there is a difference between correspondingly labeled elements that is not pointed out, and this difference results in a non-corresponding structure or function of an element for a particular embodiment, example or aspect, then the conflicting description given for that particular embodiment, example or aspect shall govern.

Locally controlled, sustained drug delivery systems (DDS) using biodegradable polymers have been actively developed since sutures made of biodegradable polymers were successfully commercialized about 40 years ago. Among all the biodegradable polymers, polylactic glycolic acid (PLGA) has shown the most potential as a drug delivery system due to its long clinical history and versatile degradation property. A number of drug delivery systems based on PLGA have already been commercialized, as an example. These products include Lupron Depot®, Risperdal Consta®, Zoladex Depot®, Decapetyl and Sandostatin LAR®, as examples. Their combined worldwide sales revenue is approximately $5 billion. There are various additional PLGA-based drug delivery system products under development, as well.

As an example, the drug release rate from PLGA microparticles can be controlled by adjusting a number of parameters, such as 1) the ratio between polylactic acid (PLA) and polyglycolic acid (PGA), 2) the molecular weight, and 3) the size of the micro-particle. In a PLGA polymer ("PLGA polymer," "PLGA"), polylactic acid is more hydrophobic compared to polyglycolic acid, for example, and subsequently hydrolyzes (i.e., degrades) slower. For example, PLGA 50:50 (PLA:PGA) exhibits a faster degradation rate than PLGA 75:25, due to preferential degradation of the glycolic acid proportion if two polymers have the same molecular weight. The PLGA polymer having a higher molecular weight exhibits a slower degradation rate than the PLGA polymer having a lower molecular weight, for example. As is known, molecular weight has a direct relationship with the polymer chain size. Higher molecular weight PLGA has a longer polymer chain and thus requires more time to degrade than PLGA having a lower molecular weight, as an example. In addition, an increase in molecular weight decreases the drug diffusion rate, and therefore the drug release rate. The size of the micro-particle also affects the rate of drug release, as an example. As the size of the micro-particle decreases, the ratio of surface area to volume of the micro-particle increases. Thus, for a given rate of drug diffusion, the rate of drug release from the micro-particle will increase with decreasing micro-particle size. Additionally, water penetration into a smaller micro-particle may be quicker due to the shorter distance from the surface to the center of the micro-particle. As an example, the property and amount of medication can also affect the rate of drug release.

Medications

As will be described throughout this disclosure below, the present invention uses medication(s) having effects on various receptors sites, such as sodium channel blockers, N-methyl-D-aspartate (NMDA) receptor antagonists, α-adrenergic receptor agonists, anti-inflammatory drugs, calcium channel blockers, or other classes of medications or their mixtures for reducing diabetic neuropathy pain, other neuropathic pains, or other chronic pains, such as back pains and joint pains, including osteoarthritis.

Sodium Channel Blocker

Sodium channels control a flow of sodium ions that can trigger excitability of pain-sensing sensors in the peripheral nervous system. Blocking the flow of sodium ions reduces pain, as an example. In addition to reducing the pain, sodium channel blockers are useful for treating a variety of other diseases described below:

Tricyclic anti-depressants (TCAs)
Anti-convulsants
Antiarrhythmics
Local anesthetics The present invention can select one or more of the above-listed sodium channel blockers described in the following sections as pain management medication(s).

TCAs

TCAs are a popular treatment choice for patients suffering from depression. TCAs may include amitriptyline, nortriptyline, desipramine, doxepin, and imipramine, as examples. The TCAs have multiple modes of action, such as inhibition of serotonin and norepinephrine reuptake from synaptic clefts, which may vary degrees of anticholinergic receptor inhibition and block sodium and calcium channels. In some embodiments, the present invention uses amitriptyline as its pain management medication. Amitriptyline demonstrated strong efficacy in reducing diabetic neuropathy pain (NNT; number of patients needed to treat for at least 50% pain relief=1.3) when taken orally. However, amitriptyline has many systemic side effects, prohibiting a broad commercial use. These side effects caused by oral administration can be reduced by the local delivery system disclosed herein.

Anti-Convulsants

Anti-convulsants treat epileptic seizures and include a diverse group of medications, such as barbiturates (e.g., phenobarbital), benzodiazepines (e.g., diazepam and lorazepam), carboxamides (e.g., carbamazepine and oxcarbazepine), fructose derivatives (e.g., topiramate), GABA analogs (e.g., pregabalin and gabapentin), hydantoins (e.g., phenytoin), sulfonamides (e.g., methazolamide) and functionalized amino acids (e.g., lacosamide). The anti-convulsants block mainly sodium and calcium channels and may enhance GABA functions. Among them, carbamazepine, oxcarbazepine, phenytoin and lacosamide are known to be potent sodium channel blockers and can thus be used in the present invention. In some embodiments, lacosamide, which is a more selective sodium channel blocker toward a small fiber neuropathy, can be used.

Antiarrhythmics

Antiarrhythmics are a group of drugs that may be used to suppress abnormal rhythms of the heart, such as atrial fibrillation, atrial flutter, ventricular tachycardia, and ventricular fibrillation. Class I antiarrhythmics function as sodium channel blockers and have three groups: Ia, Ib, and Ic. Group Ia lengthens the action potential, Group Ib shortens the action potential and Group Ic insignificantly affects the action potential. Group Ia includes quinidine, procainamide and disopyramide, as examples. Group Ib includes mexiletine, lidocaine, tocainide, and phenytoin, as examples. Group Ic includes flecainide, procainamide, moricizine and propafenone, as examples. In some embodiments, the present invention may use quinidine, procainamide, disopyramide, mexiletine, lidocaine, tocainide, phenytoin, flecainide, procainamide, moricizine, or propafenone, as an example.

Local Anesthetics

Local anesthetics are a medication used to decrease pain or sense of pain in a specific area. Local anesthetics can be administered by injecting them into the area around a nerve, for example. Local anesthetics based on sodium channel blockers include lidocaine, tetracaine, bupivacaine, and ropivacaine, as examples. In some embodiments, the present invention may use lidocaine, tetracaine, bupivacaine, or ropivacaine, as an example.

In addition to the sodium channel blockers described above, the present invention can also use other sodium channel blockers, such sumatriptan (for migraine treatment) or rufinamide (an anti-convulsant), for example.

NMDA Receptor Antagonists

It is known that NMDA receptor antagonists are effective in treating neuropathic pain. NMDA receptor antagonists may include ketamine, as an example. In some embodiments, the present invention may thus include ketamine.

α2-Adrenergic Receptor Agonist

α2-adrenergic receptor agonists have been used for decades to treat common medical conditions, such as hypertension, attention deficit hyperactivity disorder, various pain and panic disorders, symptoms of opioid, benzodiazepine, or alcohol withdrawal, and cigarette craving. However, in recent years, these drugs have also been used as a muscle relaxant, sedation, and analgesia. The α2-adrenergic receptor agonist may include clonidine, tizanidine, and dexmedetomidine. In some embodiments, the present invention may use clonidine, tizanidine, or dexmedetomidine, as an example.

Anti-Inflammatory Drugs

A variety of anti-inflammatory drugs are routinely in use for treatment of musculoskeletal pain. These anti-inflammatory drugs may reduce such pain by inhibiting prostaglandins, which lower the threshold for pain conduction and act synergistically with other agents that initiate pain, such as bradykinin, serotonin or 5-hydroxytryptamine, for example. Anti-inflammatory drugs may include a COX-2 inhibitor like celecoxib, ibuprofen, flurbiprofen, ketoprofen, and diclofenac, as examples. In some embodiments, the present invention may use a COX-2 inhibitor, such as celecoxib, ibuprofen, flurbiprofen, ketoprofen, or diclofenac, as an example.

Calcium Channel Blockers

Calcium channel blockers are vasodilators that may increase neural vascular perfusion, which may contribute to improving any ischemic neuropathy component, for example. Calcium channel blockers may include nifedipine and verapamil, as examples. In some embodiments, the present invention may use nifedipine or verapamil, as an example.

Other Medication Classes

The present invention can also use other classes of medications, such as GABA analogs (e.g., gabapentin or pregabalin), serotonin norepinephrine reuptake inhibitors (e.g., duloxetine, venlafaxine or desvenlafaxine), selective serotonin reuptake inhibitors (e.g., sertraline, fluoxetine, escitalopram, or paroxetine) or muscle relaxants (e.g., baclofen or cyclobenzaprine), for example. These classes of medications can be encapsulated into PLGA microparticles and administered individually or as a mixture with other medications described previously above.

Micro-Particles

Micro-particles represent an attractive means to achieve the desired local delivery of pain management medications. Micro-particles used herein refer to particles having sizes between 1 μm and 250 μm, preferably less than 50 μm, for example, and include microcapsules, microspheres, and other particles. Micro-particles composed of drugs or medicaments and polymers are commonly used as a sustained controlled release drug delivery system ("drug delivery system," "medicament system"), as an example. Microcapsules generally have a drug core coated with a polymer film and may be spherical or non-spherical in shape, for example. In contrast, microspheres have drugs dispersed evenly in polymer and are spherical in shape, as an example.

In some embodiments, a medication having effect on specific receptor site can be encapsulated in PLGA micro-particles individually ("PLGA formulation"). For use in patients, an individual PLGA formulation can be administered alone or as a mixture with other PLGA formulation(s). For example, lacosamide, a sodium channel blocker, can be encapsulated in PLGA micro-particles to create a formulation ("lacosamide-PLGA formulation"). Ibuprofen, an anti-inflammatory drug, can be encapsulated in PLGA micro-particles to create a second formulation ("ibuprofen-PLGA formulation"), for example. Depending on the prescription determined by a doctor, patients can be treated with the lacosamide-PLGA formulation, the ibuprofen-PLGA formulation, or a mixture of both PLGA formulations. In some embodiments, each sodium channel blocker, NMDA receptor antagonist, α2-adrenergic receptor agonist, anti-inflammatory drug, calcium channel blocker or other class of medications can be encapsulated in PLGA micro-particles to form other types of PLGA formulations. These PLGA formulations can be used individually or as multiple mixtures, depending on the prescription by the doctor, for example.

As an example, the composition of PLGA consists of equal to or more than 50% of polylactic acid (PLA). In some particular embodiments, each PLGA micro-particle may contain 1-50% of medication by weight. Drug release rate from each PLGA micro-particles can be controlled, as similarly mentioned previously above, by adjusting a number of parameters, such as: 1) ratio between polylactic acid (PLA) and polyglycolic acid (PGA) 2) molecular weight, 3) size of micro-particle, and 4) amount of encapsulated medication. The present invention teaches preparing each PLGA microsphere with a different medication having a similar drug release rate. Ideally, all PLGA microspheres with various medications will release their encapsulated medications over the same time period, ranging between one and two months, for example. To adjust their drug release rates, some PLGA microspheres may contain excipients, such as polyethylene glycol (PEG) or polyvinylpyrrolidone (PVP), for example, which can accelerate the biodegradation of micro-particles. Molecular weight of PLGA is typically between 10,000 and 150,000 Daltons and may preferably be between 25,000 to 75,000 Daltons.

Micro-Particle Fabrication

Micro-particles as used in the present invention can be prepared by microencapsulation, spray drying, precipitation, hot melt microencapsulation, co-extrusion, or precision particle fabrication (PPF), among other suitable fabrication techniques. Microencapsulation techniques use single, double, or multiple emulsion processes in combination with a solvent removal step, such as an evaporation, extraction or coacervation step. Such techniques are also the most commonly used techniques to prepare micro-particles, as an example. Thus, an advantage is that the microparticles of the present invention can be prepared using known, readily available techniques, which may reduce complex design requirements and thus lower manufacturing costs. The above techniques, including the microencapsulation techniques, can be used for a water-soluble drug, an organic solvent soluble drug and a solid powder drug. Polyesters can be processed with any one of the above techniques, as an example.

Excipients

Micro-particles as used in the present invention may also contain one or more pharmaceutically acceptable additives. The term "additive" refers to all components contained in micro-particles other than drugs or polymer and includes, but is not limited to, buffers, preservatives, and antimicrobials. The additives can also include hydrophilic materials, such as polyethylene glycol (PEG) or polyvinylpyrrolidone (PVP), which can accelerate the biodegradation of micro-particles, as an example.

Painless Microinjection Device

Conventional hypodermic needles are often used in clinical practice to deliver medications across the skin into the bloodstream. Injections by hypodermic needles are important from a clinical standpoint but are also painful. The present invention may require injections at multiple sites, for example. Painless microneedle injection devices, such as ClickSoft™ Microinjection Device by PKA SoftTouch Corp. and patches, such as Microneedle Drug Delivery System by 3M, have been developed and commercialized. The present invention can use one of these new injection methods to inject the selected medicament set at a single site or multiple sites, as an example, such that the microneedle injection device forms a part of the disclosed drug delivery system.

Treatment

According to an aspect of the present invention, a physician may compound a comprehensive set of pain management medications, such as sodium channel blockers, N-methyl-D-aspartate (NMDA) receptor antagonists, α-2 adrenergic receptor agonists, anti-inflammatory drugs, calcium channel blockers, other classes of medications or their mixtures for treatment of neuropathic pain for a specific patient, which will be described in greater detail later when referring to FIG. 9. The comprehensive set may provide regulations of multiple receptors simultaneously without significant side effects, as an advantage, which will be described in detail later below under Examples. The specific medicament compounds can be supplied to the physician or independent medicament compounds can be supplied that are designed to be combined in a specific ratio for the treatment of each patient, as an example. In this way, the medicament compound provides a treatment method which can be tailored to a prescription determined by the doctor for each patient. The physician can also include a proportion of non-medications, such as buffers, preservatives, and antimicrobials, as examples. The medicament compound and the proportion of non-medicament composites are all encapsulated in PLGA micro-particles having a critical size between 1 μm and 50 μm for controlled, sustained release of drug over 2-8 weeks. Once a doctor prescribes a set of pain management medications, the prescribed medication(s) can be administered individually or as mixtures by a commercial painless microneedle patch or injection device, mentioned previously above. Thus, an advantage is that the user-friendly injection method may enable injecting a small amount of pain management medications at multiple sites, which may thus enhance the efficacy of treatment.

EXAMPLES

In order to demonstrate the benefit of treating various pains associated with diabetic neuropathy by using multiple pain management medications, as disclosed above, five specific pain management medications encapsulated in PLGA microspheres were developed, to be outlined below. Furthermore, various experiments were conducted, including an efficacy test using a diabetic neuropathy pain model applied in rats, for example, to illustrate the effectiveness of the pain management medications as a medicament set, as will be described in detail below.

As mentioned above, five pain management medications encapsulated in PLGA microspheres were prepared, whose characterizations will be described in the following section. The five pain management medications that were prepared and studied include celecoxib (CXB, an anti-inflammatory drug), lidocaine (LDC, a local anesthetic and sodium channel blocker drug), amitriptyline (AMT, a tricyclic antidepressant drug), carbamazepine (CBZ, an anti-convulsant and sodium channel blocker drug) and clonidine (CLO, an α-2 adrenergic receptor anti-agonist drug). As an example, the five aforementioned pain management medications encapsulated in PLGA released their respective encapsulated medications from each PLGA microsphere for about two weeks. In order to obtain a 14-day release profile, the molecular weight of PLGA for each pain management medication was optimized (i.e., selectively proportioned), for example.

As mentioned above, the first studied pain management medication was celecoxib. In order to prepare the celecoxib-loaded PLGA microsphere ("CXB-30 kda"), about 1 gram (g) of PLGA having a molecular weight (MW) of 30 kilodaltons (kda) and a 50:50 PLA to PGA molar ratio was dissolved in about 9 milliliters (mL) of dichloromethane (DCM). The polymer solution was stirred at room temperature for about 1 hour to completely dissolve the PLGA. Then, about 100 milligrams (mg) of celecoxib was added to the polymer solution and stirred for about 10 minutes. The resultant solution, now in an oil phase, was poured into a dispersion phase tank (e.g., Shirasu Porous Glass (SPG) membrane machine manufactured by MCTech) and then pressed through a ceramic membrane having a pore size of about 20 micrometers (μm), using nitrogen gas, into a continuous phase tank filled with a 4% PVA aqueous solution. The aforementioned process was carried out for about 2 hours. The resultant aqueous phase solution was collected in a glass beaker and stirred with a propeller stirrer for about 4 hours at room temperature to remove any remaining DCM. Then, 500 mL of cold deionized (DI) water was added to the microsphere solution and filtered onto 20 μm filter paper or centrifuged at 3,000 rotations per minute (rpm) for 5 minutes, after cooling down for about 6 hours at 4° Celsius (C), which was followed by a washing with 1 L of cold water. The collected pellets/spheres were freeze-dried for 24-48 hours and subsequently dried for 72 hours at 39° C. in a vacuum oven.

The above-described preparation process was similarly carried out for each of the lidocaine and carbamazepine-loaded PLGA microspheres pain management medications. As such, for the lidocaine-loaded PLGA microsphere ("LDC-30 kda" or "LDC-40 kda"), 1 g of PLGA having a MW of 30 kda or 40 kda and a 50:50 PLA:PGA molar ratio was dissolved in 5 mL of DCM by stirring at room temperature for 1 hour. Then about 200 mg of lidocaine was added to the polymer solution and stirred for 10 minutes. The remaining preparation steps may follow those described previously above for the preparation of the celecoxib-loaded PLGA microsphere. Alternatively, for the carbamazepine-loaded PLGA microsphere ("CBZ-30 kda" or "CBZ-40 kda"), about 200 mg of carbamazepine was added into the original PLGA and subsequently stirred for 10 minutes. Similarly, the remaining preparation steps for the carbamazepine-loaded PLGA microsphere may follow those described previously above for the preparation of the celecoxib-loaded PLGA microsphere. It should be noted, however, for the final preparation step, the collected pellets may be dried for 72 hours at either 36° C. or 39° C. in a vacuum oven.

Finally, the preparation of the amitriptyline-loaded and the clonidine-loaded PLGA microspheres were carried out as follows. For the amitriptyline-based pain management medication, about 200 mg of amitriptyline-hydrochloride (AMT-HCl) was dissolved in 6 mL of DCM, with 300 microliters (μL) or 150 μL of triethylamine being added to neutralize, followed by 1.5 hours of stirring. For the clonidine-based pain management medication, about 100 mg of clonidine hydrochloride was dissolved in 6 mL of DCM, with 300 μL or 150 μL of triethylamine being added to neutralize, followed by about 1.5 hours of stirring. To both of the aforementioned solutions, about 1 g of PLGA, having a 30 kda or 40 kda MW and a 50:50 PLA:PGA molar ratio, was added. The mixture, now in oil phase, was poured into the dispersion phase tank of the SPG membrane machine and pressed through a ceramic membrane (pore size of 20 μm), using nitrogen gas, and into the continuous phase tank filled with 4% PVA aqueous solution (pH 10-11). The process was carried out for around 2 hours. The resultant aqueous phase was collected in a glass beaker and stirred with a propeller stirrer for 6 hours at room temperature to remove the DCM. Then, cold DI water (500 mL) was added to the microsphere solution, which was then filtered on 20 μm filter paper or centrifuged at 3,000 rpm for 5 minutes, after cooling down for 4-6 hours at 4° C., which was followed by a washing with cold water (1 L). The collected pellets were freeze-dried for 48 hours and dried for 48-72 hours at 39° C. in a vacuum oven.

In Vitro Release Study

As an example, each of the five previously described pain management medications was subject to an in vitro release study, which was carried out using a sample-and-separate method, to quantify the rate of drug delivery. Briefly, about 5-200 mg of the microsphere sample (n=3) was carried in a 100 mL conical flask and dispersed into 50 mL of a release medium having 0.5% Tween and 0.1% sodium azide in either PBS at pH 7.4 or PBS at PH 7.4, for example. The flasks containing each sample were then placed in an orbital agitating incubator set at 37° C. and rotated at 100 rpm. At certain time points over the two-week study (1 hour, 3 hours, 1 day, 2 days, 4 days, 7 days, 9 days, 11 days, 14 days), 40 mL of the medium was taken and centrifuged at 3,000 rpm for 2 minutes (each time). From the supernatant, 30 mL was pipetted out and replaced by the same amount of the fresh media. In the collected supernatant, the content of the released pain management medication was analyzed by High Performance Liquid Chromatography (HPLC). The release profiles of the five pain management medications are shown in FIGS. 1-5, respectively, which will be described in detail below.

FIG. 1 is a plot 110 illustrating the release profile of a lidocaine-loaded PLGA microsphere (LDC-30 kda and LDC-40 kda), according to an aspect. As mentioned previously above, the lidocaine-loaded PLGA microsphere ("microsphere," "MS") was prepared using lidocaine having either a 30 kda MW or a 40 kda MW, whose release curves are both shown in FIG. 1 at 104 and 105, respectively. As shown in the plot 110 of FIG. 1, the release profile of the lidocaine-loaded PLGAMS illustrates the cumulative release of the LDC measured as a percentage (%), as indicated on the y-axis, versus the experimental time period measured in days, as indicated on the x-axis, for example. As mentioned previously above, the release profile shown in FIG. 1 for lidocaine illustrates, essentially, the duration of time it takes for a particular percentage of the drug encapsulated in the PLGA MS to be released (i.e., delivered). As shown by the plot 110, by percentage, the release of LDC having a MW of 30 kda (at 104) released quicker than LDC having a MW of 40 kda (at 105), as an example. As described previously in this disclosure above, the release rate may be inversely proportional to the MW of the drug in question, which can be seen by comparison of the release curves 104 and 105, for example. As shown, by only the first day, a majority of both concentrations of LDC (30 kda and 40 kda) was released, with over 60% of LDC-40 kda being released and over 70% of LDC-30 kda being released, as shown by 105 and 104, respectively. As further illustrated by the plot 110, a larger majority (over 90%) of LDC-30 kda, at 104, was released at about the 7-day mark, as shown, while that of LDC-40, at 105, was released a few days later at about the 10-day mark, as an example. Thus, as illustrated in FIG. 1, the drug delivery time (i.e., the release rate) for lidocaine encapsulated in PLGA microspheres is well within the 2-8 week release period target mentioned previously in this disclosure.

Figure 2:
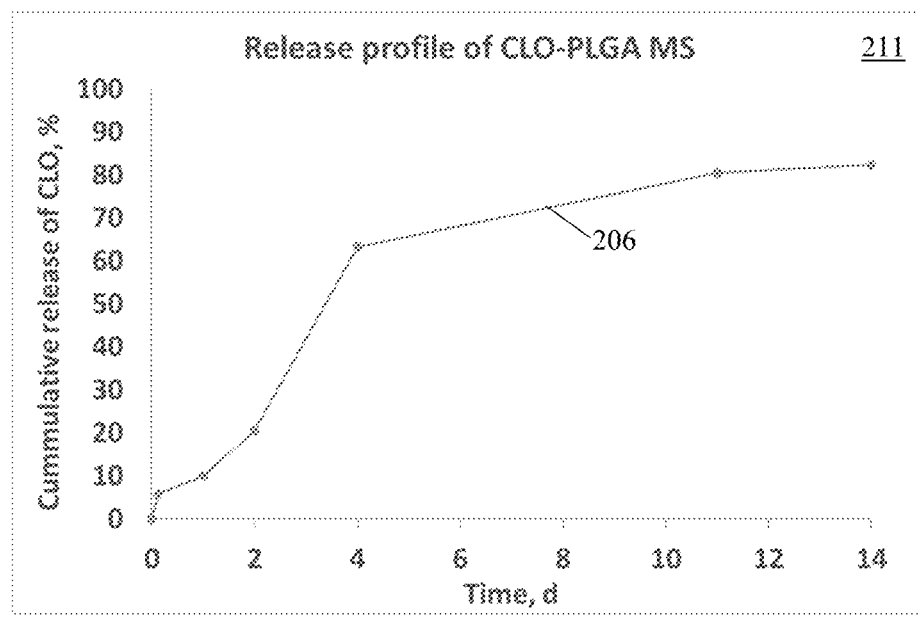
FIG. 2 is a plot illustrating the release profile of a clonidine-loaded PLGA microsphere (CLO-30 kda), according to an aspect.

FIG. 2 is a plot 211 illustrating the release profile of a clonidine-loaded PLGA microsphere (CLO-30 kda), according to an aspect. As mentioned previously above, the clonidine-loaded PLGA microsphere was prepared using clonidine having a 30 kda MW, whose release curve is shown in FIG. 2 at 206, as an example. As shown in the plot 211 of FIG. 2, the release profile of the clonidine-loaded PLGA MS illustrates the cumulative release of the CLO measured as a percentage (%), as indicated on the y-axis, versus the experimental time period measured in days, as indicated on the x-axis, for example. As mentioned previously above, the release profile of 211 shown in FIG. 2 for clonidine illustrates, essentially, the duration of time it takes for a particular percentage of the drug encapsulated in the PLGA MS to be released (i.e., delivered). As shown by the plot 211, by percentage, the release of CLO having a MW of 30 kda (at 206) occurred over a 14-day period, as indicated on the x-axis, where a majority (over 60%) of the CLO was released within the first 4 days. Subsequently, as shown, the remaining majority of the CLO was more steadily released over the remaining experiment time period, with over 80% of the CLO being released by the $14^{th}$ day, as shown by 206, for example. Thus, as illustrated in FIG. 2, the drug delivery time (i.e., the release rate) for clonidine encapsulated in PLGA microspheres is well within the 2-8-week release period target mentioned previously in this disclosure.

Figure 3:
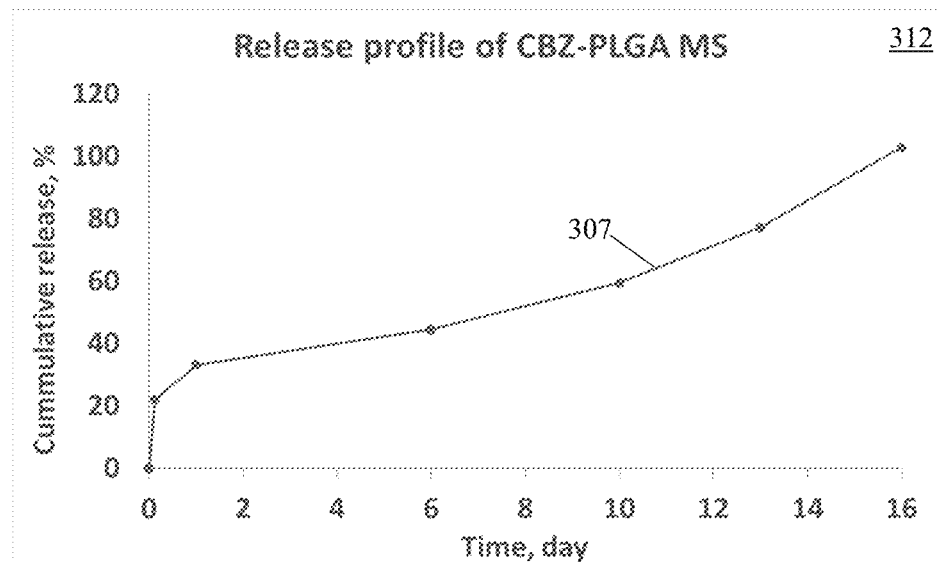
FIG. 3 is a plot illustrating the release profile of a carbamazepine-loaded PLGA microsphere (CBZ-30 kda), according to an aspect.

FIG. 3 is a plot 312 illustrating the release profile of a carbamazepine-loaded PLGA microsphere (CBZ-30 kda), according to an aspect. As mentioned previously above, the carbamazepine-loaded PLGA microsphere was prepared using carbamazepine having a 30 kda MW, whose release curve is shown in FIG. 3 at 307, as an example. As shown in the plot 312 of FIG. 3, the release profile of the carbamazepine-loaded PLGA MS illustrates the cumulative release of the CBZ measured as a percentage (%), as indicated on the y-axis, versus the experimental time period measured in days, as indicated on the x-axis, for example. As mentioned previously above, the release profile of 312 shown in FIG. 3 for carbamazepine illustrates, essentially, the duration of time it takes for a particular percentage of the drug encapsulated in the PLGA MS to be released (i.e., delivered). As shown by the plot 312, by percentage, the release of CBZ having a MW of 30 kda (at 307) occurred over a 16-day period, as indicated on the x-axis, where a majority (over 60%) of the CBZ was released within the first 10 days. Subsequently, as shown, the remaining majority of the CBZ was more steadily released over the remaining experiment time period, with almost 100% of the CBZ being released by the $16^{th}$ day, as shown by 307, for example. Thus, as illustrated in FIG. 3, the drug delivery time (i.e., the release rate) for carbamazepine encapsulated in PLGA microspheres is well within the 2-8-week release period target mentioned herein above.

Figure 4:
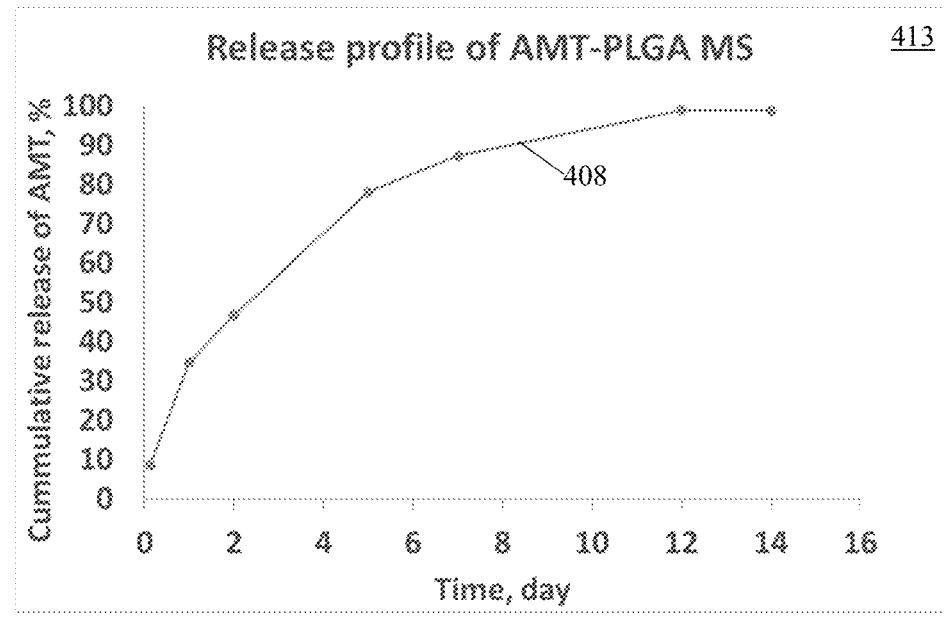
FIG. 4 is a plot illustrating the release profile of an amitriptyline-loaded PLGA microsphere (AMP-30 kda), according to an aspect.

FIG. 4 is a plot 413 illustrating the release profile of an amitriptyline-loaded PLGA microsphere (AMP-30 kda), according to an aspect. As mentioned previously above, the amitriptyline-loaded PLGA microsphere was prepared using amitriptyline having a 30 kda MW, whose release curve is shown in FIG. 4 at 408, as an example. As shown in the plot 413 of FIG. 4, the release profile of the amitriptyline-loaded PLGA MS illustrates the cumulative release of the AMP measured as a percentage (%), as indicated on the y-axis, versus the experimental time period measured in days, as indicated on the x-axis, for example. As mentioned previously above, the release profile of 413 shown in FIG. 4 for amitriptyline illustrates, essentially, the duration of time it takes for a particular percentage of the drug encapsulated in the PLGA MS to be released (i.e., delivered). As shown by the plot 413, by percentage, the release of AMT having a MW of 30 kda (at 408) occurred over a 16-day period, as indicated on the x-axis, where a majority (over 60%) of the AMT was released within the first 3 days. Subsequently, as shown, the remaining majority of the AMT was more steadily released over the remaining experiment time period, with over 90% of the AMT being released around the $12^{th}$ day, as shown by 408, for example. Thus, as illustrated in FIG. 4, the drug delivery time (i.e., the release rate) for amitriptyline encapsulated in PLGA microspheres is well within the 2-8-week release period goal outlined previously above.

Figure 5:
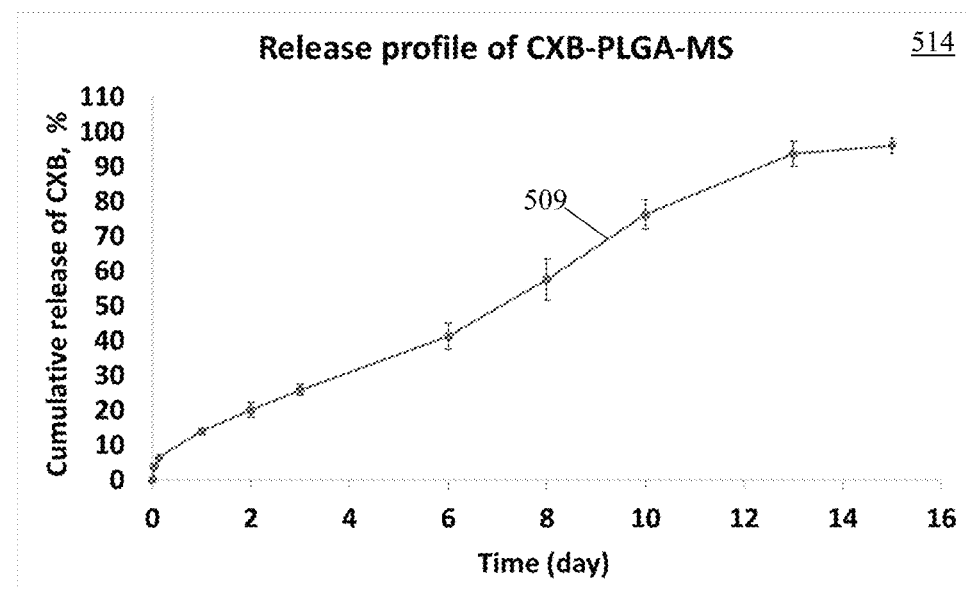
FIG. 5 is a plot illustrating the release profile of a celecoxib-loaded PLGA microsphere (CXB-30 kda), according to an aspect.

FIG. 5 is a plot 514 illustrating the release profile of a celecoxib-loaded PLGA microsphere (CXB-30 kda), according to an aspect. As mentioned previously above, the celecoxib-loaded PLGA microsphere was prepared using celecoxib having a 30 kda MW, whose release curve is shown in FIG. 5 at 509, as an example. As shown in the plot 514 of FIG. 5, the release profile of the celecoxib-loaded PLGA MS illustrates the cumulative release of the CXB measured as a percentage (%), as indicated on the y-axis, versus the experimental time period measured in days, as indicated on the x-axis, for example. As mentioned previously above, the release profile of 514 shown in FIG. 5 for celecoxib illustrates, essentially, the duration of time it takes for a particular percentage of the drug encapsulated in the PLGA MS to be released (i.e., delivered). As shown by the plot 514, by percentage, the release of CXB having a MW of 30 kda (at 509) occurred over a 16-day period, as indicated on the x-axis, where a majority (about 60%) of the CXB was released within around 8 days. Subsequently, as shown, the remaining majority of the CXB was more steadily released over the remaining experiment time period, with over 90% of the AMT being released around the 13$^{th}$ day, as shown by 509, for example. Thus, as illustrated in FIG. 5, the drug delivery time (i.e., the release rate) for celecoxib encapsulated in PLGA microspheres is well within the 2-8-week release period target provided previously in this disclosure above.

As mentioned previously above, the content of each of the released pain management medications was analyzed by High Performance Liquid Chromatography (HPLC). The preparation of the calibration curve for each pain management medication, for example, and the analysis by HPLC were carried out as follows. A stock solution (2-10 mg/mL) of celecoxib, carbamazepine, lidocaine, clonidine, or amitriptyline was prepared in an organic solvent, such as acetonitrile or methanol (HPLC grade). Then, using the stock solution, a series of concentrations of each medication solution (0.08, 0.4, 2, 10, 50, and 100 μg/mL) were obtained and were each filtered through a 0.45 μm syringe filter. As a mobile phase, acetonitrile and 0.1% phosphoric acid solution at various ratios (60:40, 50:50, and 20:80) were applied. Subsequently, analysis of active pharmaceutical ingredients (APIs) was carried out by the HPLC system with a C18 column (e.g., Agilent Poroshell 120 EC-C18; 4.6 mm×150 mm, 4 μm) connected to an ultraviolet (UV) detector. By this method, CXB was detected at 260 nanometers (nm) (retention time of 5.2 minutes), CBZ was detected at 220 nm (retention time of 2.3 minutes), AMT was detected at 254 nm (retention time of 2.7 min), CLO was detected at 220 nm (retention time of 1.89 min) and LDC was detected at 210 nm (retention time of 3.9 min), for example. In order to determine the content of the respective medications in a given microsphere, certain amounts of API-PLGA-MS were weighed and dissolved in acetonitrile or methanol (MeOH) via 10-minute sonication. Each disrupted solution was then diluted with mobile phase and measured by HPLC. The drug encapsulation efficiency (EE) and drug loading content (LC) were calculated by the following equations:

$$EE(\%) = \frac{\text{Weight of found Drug}}{\text{Weight of feed Drug}} \times 100$$

$$LC(\%) = \frac{\text{Weight of found Drug}}{\text{Weight of feed Drug} + \text{Feed } PLGA} \times 100$$

The calculated drug encapsulation efficiency and drug loading content of the five pain management medications encapsulated in PLGA are summarized in Table 1 below, along with their respective yields in percent, size in micrometers, and release time in days (shown previously in FIGS. 1-5, for example).

TABLE 1

Characteristics of drug-loaded PLGA-microspheres

| APIs | Name | Yield (%) | EE (%) | LC (%) | Size (μm) | Release over 80% |
|---|---|---|---|---|---|---|
| Celecoxib (CXB) | CXB-30 kda | 86.4 | 87.3 | 8.73 | 20-35 | 14 day |
| Lidocaine (LDC) | LDC-30 kda | 74.2 | 26.4 | 5.3 | 35-48 | 7 day |
|  | LDC-40 kda | 81.5 | 25.7 | 5.1 | 26-46 | 10 day |
| Amitriptyline (AMT) | AMT-30 kda | 81.5 | 64.03 | 12.8 | 35-46 | 14 day |
|  | AMT-40 kda | 78.1 | 78.7 | 15.7 | 24-42 | 16 day |
| Carbamazepine (CBZ) | CBZ-30 kda | 63.5 | 33.9 | 6.78 | 32-42 | 16 day |
|  | CBZ-40 kda | 73.6 | 37.2 | 7.45 | 32-39 | Over 16 day |
| Clonidine (CLO) | CLO-30 kda | 82.0 | 18.4 | 1.84 | 27-42 | 14 day |
|  | CLO-4o kda | 82.1 | 14.4 | 1.44 | 27-39 | Over 14 day |

As shown in Table 1 above, each of the five pain management medications encapsulated in the PLGA microspheres possess a relatively high yield percentage, with CXB having the highest at about 86.4% and CBZ (with 30 kda MW) having the lowest at about 63.5%, for example. As shown by the above yield percentages, the five drugs are efficiently delivered via the PLGA microspheres.

Rat Efficacy Test

A sciatic nerve constriction model of neuropathic pain in rats (i.e., chronic compression of sciatic nerve to create pain) was used to evaluate the efficacy of each of the five pain management medications described above against a diluent carboxymethyl cellulose (CMC) solution-treated control. The efficacy was determined via mechanical withdrawal threshold using a von Frey aesthesiometer test of each hind paw in the test rats (von Frey test, to be described below) and via a thermal hyperalgesia paw withdrawal latency response test using thermal stimulation by heat plate instrument (hot plate test, to be described below).

As an example, the test rats were separated into six groups (e.g., four rats per group), with each group being assigned to be dosed with either the diluent CMC solution (the control) or with a carefully selected effective amount of one of the five pain management medications described above. The effective dose for each group of test rats were assigned as follows:

Group 1 was assigned to dosing with diluent CMC solution (control)

Group 2 was assigned to dosing with PLGA-Amitriptyline (AMT-30 kda) at 0.5 mg/kg Group 3 was assigned to dosing with PLGA-clonidine (CLO-30 kda) at 0.06 mg/kg Group 4 was assigned to dosing with PLGA-carbamazepine (CBZ-30 kda) at 5 mg/kg Group 5 was assigned to dosing with PLGA-lidocaine (LDC-40 kda) at 10 mg/kg Group 6 was assigned to dosing with PLGA-celecoxib (CXB-30 kda) at 1.5 mg/kg As mentioned above, the rat efficacy test comprises two separate tests, one being the von Frey test and the other being the hot plate test, which were conducted in two separate phases. These two tests were conducted in Phase I of the study, which was aimed at evaluating and comparing the ability of the five different pain management medications to treat and control neuropathic pain. After analyzing the outcome of the Phase I study, a second phase, called Phase II, evaluated, and compared the efficacy of medication combinations consisting of a mixture of two (celecoxib and carbamazepine) or three (celecoxib, carbamazepine, and lidocaine) of the five pain management medications. Phases I and II will be described herein in the following sections.

Phase I Study

Von Frey Test

As mentioned above, the von Frey test was the first test conducted during Phase I of the rat efficacy study. For this portion of the experiment, von Frey tests were conducted on five occasions as follows: at pre-operation (prior to sciatic nerve constriction procedure), post-operation after creating chronic compression of sciatic nerve but prior to medication treatment, and three times post-operation on Day 0 (the day of dosing at 3+ hours post dose), Day 4 post dosing, and Day 9 post dosing. Mean values and the standard error of the mean (SEM) values for the treated limb (left) and the contra-lateral limb (right) of each rat of each Group were calculated, as well as the percent change from control limb, and the percent change from baseline for each Group. Treatment was initiated when the test subjects (i.e., rats) presented with chronic sciatic pain consistent with the rat model as published in literature. Each animal was dosed on Day 0 via a single bolus 300 µL subcutaneous injection close to the sciatic nerve procedure flank, for example. A summary of the von Frey test results for each of the test rat groups is shown in FIG. 6, which will be described in detail below.

Figure 6:
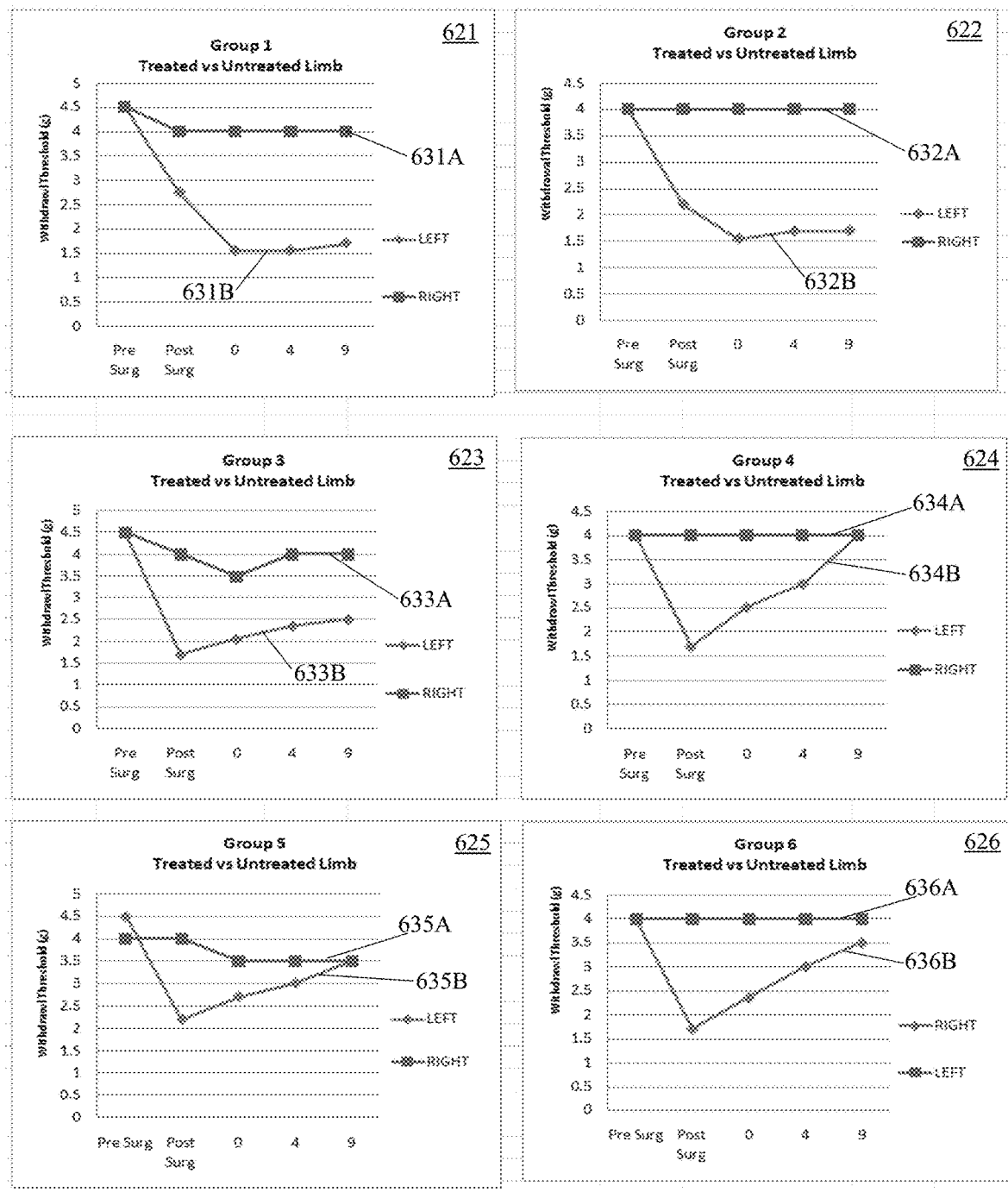
FIG. 6 is a plot summary illustrating the von Frey test results for Groups 1-6, according to an aspect.

FIG. 6 is a plot summary illustrating the von Frey test results for Groups 1-6 conducted during the Phase I Study, according to an aspect. As mentioned previously above, the test rats were divided into six groups, with each group receiving a different dose of treatment, as an example. The von Frey aesthesiometer was used on each rat of each group to assess the mechanical withdrawal threshold, measured in grams-force ((g) in FIG. 6), for measuring paw withdrawal, for example, such that to analyze each drug's effectiveness at withstanding pain, which may thus determine the drug's efficacy. As will be described below, the outcomes of the von Frey tests compare the treated limbs of the test rats with the untreated limbs, as an example.

As shown in FIG. 6, the plot 621 illustrates the mean von Frey test results for Group 1 of the test rats, particularly for the right hind paw, shown at 631A, and the left hind paw, shown at 631B, for each rat of Group 1, as an example. As discussed above, each test rat of Group 1 received a dose of diluent CMC solution injected into the left hind paw (i.e., the treated limb), and nothing was injected into the right contralateral paw (i.e., the untreated limb), as similarly indicated in plot 621. In this way, the right untreated limb, shown at 631A, functions as the baseline (i.e., healthy limb), and the left treated limb, shown at 631B, functions as the control, against which the remaining groups of treated test rats were compared. As shown, the plot 621 plots the mean withdrawal threshold, measured in grams-force (g), as indicated on the y-axis, at certain time points after dosing, described in the plot legend 620, as indicated on the x-axis, as an example. As shown, the mean withdrawal threshold, shown at 631B, after dosing the left hind paw, remained relatively stagnant, even after 9 days of drug treatment with the diluent CMC solution. Thus, based on the plot of 621, the treatment of the left paw with diluent CMC solution shows relatively no efficacy, and therefore no effectiveness for pain treatment. Thus, the efficacy of each of the five medications tested shall be compared with the low/non-existent efficacy shown by 631B in plot 621, which will be discussed in detail below.

As shown in FIG. 6, the plot 622 illustrates the mean von Frey test results for Group 2 of the test rats, particularly for the right hind paw, shown at 632A, and the left hind paw, shown at 632B, for each rat of Group 2, as an example. As discussed above, each test rat of Group 2 received a dose of PLGA-Amitriptyline (AMT-30 kda) at 0.5 mg/kg injected into the left hind paw (i.e., the treated limb), and as in Group 1, the right hind paw was left untreated (i.e., as the untreated limb), as similarly indicated in plot 622. In this way, the right untreated limb, shown at 632A, functions as the baseline (i.e., healthy limb), and the left treated limb, shown at 632B, functions as the variable for observing the effectiveness of the amitriptyline-based medication. As shown, the plot 622 plots the mean withdrawal threshold, measured in grams-force (g), as indicated on the y-axis, at certain time points after dosing, described in the plot legend 620, as indicated on the x-axis, as previously mentioned above. As shown, the mean withdrawal threshold, shown at 632B, after dosing the left hind paw, increased slightly, but little improvement was seen between 4 and 9 days of drug treatment with the PLGA-amitriptyline. Thus, based on the plot of 622, the treatment of the left paw with PLGA-amitriptyline shows some improvement in efficacy compared to that of the diluent CMC solution of the control Group 1, but overall shows little to no effectiveness for pain treatment. Thus, PLGA-amitriptyline having a 30 kda MW and injected at 0.5 mg/kg improves upon the control but shows little effectiveness alone as a treatment for pain.

As shown in FIG. 6, the plot 623 illustrates the mean von Frey test results for Group 3 of the test rats, particularly for the right hind paw, shown at 633A, and the left hind paw, shown at 633B, for each rat of Group 3, as an example. As discussed above, each test rat of Group 3 received a dose of PLGA-clonidine (CLO-30 kda) at 0.06 mg/kg injected into the left hind paw (i.e., the treated limb), and as in Group 1, the right hind paw was left untreated (i.e., as the untreated limb), as similarly indicated in plot 623. In this way, the right untreated limb, shown at 633A, functions as the baseline (i.e., healthy limb), and the left treated limb, shown at 633B, functions as the variable for observing the effectiveness of the clonidine-based medication. As shown, the plot 623 plots the mean withdrawal threshold, measured in grams-force (g), as indicated on the y-axis, at certain time points after dosing, described in the plot legend 620, as indicated on the x-axis, as previously mentioned above. As shown, the mean withdrawal threshold, shown at 633B, after dosing the left hind paw, increased steadily, but improvement slowed and thus plateaued after 9 days of drug treatment with the PLGA-clonidine. Thus, based on the plot of 623, the treatment of the left paw with PLGA-clonidine shows improvement in efficacy compared to that of the diluent CMC solution of the control Group 1, but overall shows relatively little effectiveness for pain treatment. Thus, PLGA-clonidine having a 30 kda MW and injected at 0.06 mg/kg improves upon the control and demonstrates partial efficacy but shows little effectiveness alone as a treatment for pain.

As shown in FIG. 6, the plot 624 illustrates the mean von Frey test results for Group 4 of the test rats, particularly for the right hind paw, shown at 634A, and the left hind paw, shown at 634B, for each rat of Group 4, as an example. As discussed above, each test rat of Group 4 received a dose of PLGA-carbamazepine (CBZ-30 kda) at 5 mg/kg injected into the left hind paw (i.e., the treated limb), and as in Group 1, the right hind paw was left untreated (i.e., as the untreated limb), as similarly indicated in plot 624. In this way, the right untreated limb, shown at 634A, functions as the baseline (i.e., healthy limb), and the left treated limb, shown at 634B, functions as the variable for observing the effectiveness of the carbamazepine-based medication. As shown, the plot 624 plots the mean withdrawal threshold, measured in grams-force (g), as indicated on the y-axis, at certain time points after dosing, described in the plot legend 620, as indicated on the x-axis, as previously mentioned above. As shown, the mean withdrawal threshold, shown at 634B, after dosing the left hind paw, increased significantly after dosing (at 0 on the x-axis) and continued to steadily increase until the left hind paw was effectively healthy (e.g., substantially pain-free) again, shown by the intersection of curves 634A and 634B after 9 days, for example. Thus, based on the plot of 624, the treatment of the left paw with PLGA-carbamazepine shows significant improvement in efficacy compared to that of the diluent CMC solution of the control Group 1, and therefore shows great effectiveness for pain treatment. Thus, PLGA-carbamazepine having a 30 kda MW and injected at 5 mg/kg improves upon the control and demonstrates efficacy, and thus shows great effectiveness alone as a treatment for pain.

As shown in FIG. 6, the plot 625 illustrates the mean von Frey test results for Group 5 of the test rats, particularly for the right hind paw, shown at 635A, and the left hind paw, shown at 635B, for each rat of Group 5, as an example. As discussed above, each test rat of Group 5 received a dose of PLGA-lidocaine (LDC-40 kda) at 10 mg/kg injected into the left hind paw (i.e., the treated limb), and as in Group 1, the right hind paw was left untreated (i.e., as the untreated limb), as similarly indicated in plot 625. In this way, the right untreated limb, shown at 635A, functions as the baseline (i.e., healthy limb), and the left treated limb, shown at 635B, functions as the variable for observing the effectiveness of the lidocaine-based medication. As shown, the plot 625 plots the mean withdrawal threshold, measured in grams-force (g), as indicated on the y-axis, at certain time points after dosing, described in the plot legend 620, as indicated on the x-axis, as previously mentioned above. As shown, the mean withdrawal threshold, shown at 635B, after dosing the left hind paw, increased significantly after dosing (at 0 on the x-axis) and continued to steadily increase until the left hind paw was effectively healthy (e.g., substantially pain-free) again, shown by the intersection of curves 635A and 635B after 9 days, for example. Thus, based on the plot of 625, the treatment of the left paw with PLGA-lidocaine shows significant improvement in efficacy compared to that of the diluent CMC solution of the control Group 1, and therefore shows great effectiveness for pain treatment. Thus, PLGA-lidocaine having a 40 kda MW and injected at 10 mg/kg improves upon the control and demonstrates efficacy, and thus shows great effectiveness alone as a treatment for pain.

As shown in FIG. 6, the plot 626 illustrates the mean von Frey test results for Group 6 of the test rats, particularly for the right hind paw, shown at 636A, and the left hind paw, shown at 636B, for each rat of the final Group 6, as an example. As discussed above, each test rat of Group 6 received a dose of PLGA-celecoxib (CXB-30 kda) at 1.5 mg/kg injected into the left hind paw (i.e., the treated limb), and as in Group 1, the right hind paw was left untreated (i.e., as the untreated limb), as similarly indicated in plot 626. In this way, the right untreated limb, shown at 636A, functions as the baseline (i.e., healthy limb), and the left treated limb, shown at 636B, functions as the variable for observing the effectiveness of the celecoxib-based medication. As shown, the plot 626 plots the mean withdrawal threshold, measured in grams-force (g), as indicated on the y-axis, at certain time points after dosing, described in the plot legend 620, as indicated on the x-axis, as previously mentioned above. As shown, the mean withdrawal threshold, shown at 636B, after dosing the left hind paw, increased significantly after dosing (at 0 on the x-axis) and continued to steadily increase until the left hind paw was relatively healthy (e.g., somewhat pain-free) again, shown by the proximity of curves 636A and 636B after 9 days, for example. Thus, based on the plot of 626, the treatment of the left paw with PLGA-celecoxib shows significant improvement in efficacy compared to that of the diluent CMC solution of the control Group 1, and therefore shows effectiveness for pain treatment. Thus, PLGA-celecoxib having a 30 kda MW and injected at 1.5 mg/kg improves upon the control and demonstrates efficacy, and thus shows effectiveness alone as a treatment for pain.

Thus, as demonstrated by the mean von Frey test results summarized in FIG. 6 and discussed above, Groups 4, 5, and 6 treated with PLGA-carbamazepine, PLGA-lidocaine, and PLGA-celecoxib, respectively, increased the test rats' pain tolerance, and thus demonstrated efficacy, as compared to the control group. Thus, as stated above, these three medications may function effectively and efficiently as individual treatments for peripheral neuropathy pain. Thus, an advantage of the disclosed method is that neuropathic pain may effectively and efficiently be treated in a timely manner.

Hot Plate Test

As mentioned previously above, the hot plate test was the second test conducted during Phase I of the rat efficacy study. For this portion of the experiment, hot plate tests were conducted on five occasions as follows: at pre-operation (prior to sciatic nerve constriction procedure), post-operation after creating chronic compression of sciatic nerve but prior to medication treatment, and three times post-operation on Day 1 post dosing, Day 5 post dosing, and Day 10 post dosing. Mean values and the standard error of the mean (SEM) values, and percent change from baseline, were calculated for each test group for each occasion. The hot plate tests, as an example, analyzed the thermal hyperalgesia paw withdrawal latency response using thermal stimulation of the test rats. The paw withdrawal latency response observed the thermal stimulation applied to induce a nociceptive response (e.g., hind paw lick, flinch, or jump) for each test group, for example. The nociceptive response, for example, may thus serve as an indicator for the pain being experienced by the test rats.

Body weights were also taken on three occasions at pre-operation prior to sciatic nerve constriction procedure, at time of test or control article dosing Day 0, and at termination at Day 10 post dose.

Treatment was initiated when the test subjects (i.e., rats) presented with chronic sciatic pain consistent with the rat model as published in literature. Five groups of 4 rats per group, as an example, were treated with a designated pain management medication (one of the five previously described medications) and one group was treated with diluent CMC solution (the treated control). Each animal was dosed on Day 0 via a single bolus 300 μL subcutaneous injection close to the sciatic nerve procedure flank. A summary of the hot plate test results for each of the test rat groups is shown in FIG. 7, which will be described in detail below.

Figure 7:
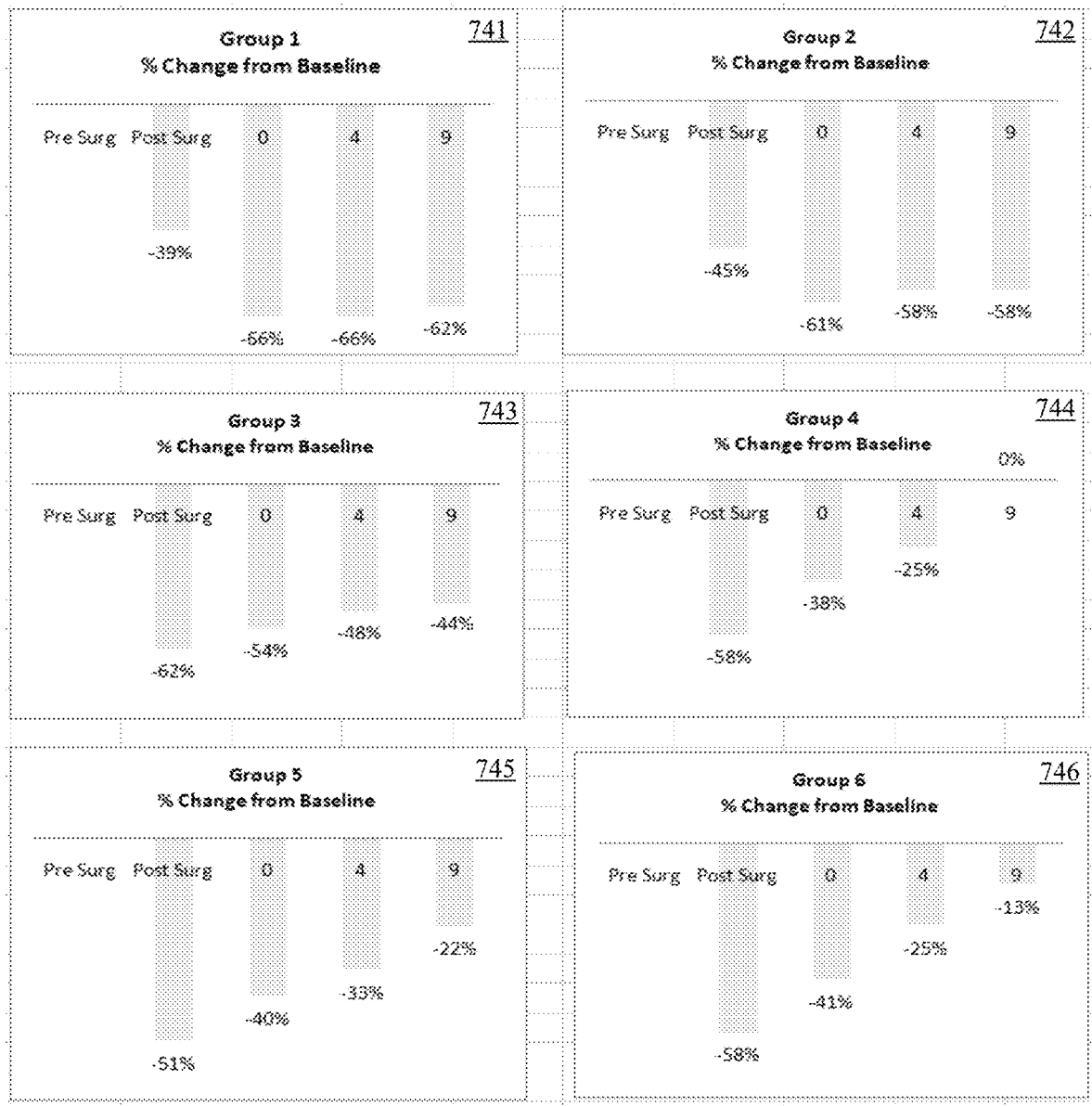
FIG. 7 is a bar graph summary illustrating the hot plate results for Groups 1-6, according to an aspect.

FIG. 7 is a bar graph summary illustrating the hot plate test results for Groups 1-6 conducted during the Phase I study, according to an aspect. As mentioned previously above, the hot plate tests measured, as a percent change from baseline, the paw withdrawal latency response due to thermal stimulation for each group of test rats, as an example, which are summarized in plots 743-756, as shown. The baseline, for example, is the paw withdrawal latency response of the test rats prior to sciatic nerve compression (labeled Pre Surg in FIG. 7). Again, as indicated in the plot legend 720, the hot plate tests were conducted on the rats of each group were taken five times over the experimental timeline, with each plot 743-756 reflecting the percent change of the rats' paw withdrawal latency response with respect to the baseline (withdrawal latency response prior to chronic compression of sciatic nerve, for example), which will be described in detail below.

Again, as described previously when referring to FIG. 6, Groups 1, 2, 3, 4, 5, and 6 were treated with diluent CMC solution (control), PLGA-amitriptyline, PLGA-clonidine, PLGA-carbamazepine, PLGA-lidocaine, and PLGA-celecoxib, respectively. As shown in the plot 741, the hot plate test results indicate that, on average, Group 1 rats (the control group) experienced significantly high levels of withdrawal response change, particularly a decrease in the withdrawal latency response, as a result of their respective neuropathic pains, for example. As shown in the plot 742 of FIG. 7, Group 2, which was treated with PLGA-amitriptyline, demonstrated a decline in mean withdrawal latency response, similar in percent change for each of those shown for Group 1 in plot 741, as an example. The mean withdrawal latency response of Group 2 indicated that the test rats demonstrated little improvement in pain tolerance, which was in marked contrast to the increase in withdrawal latency response observed for the control group (change from −66% to −62% in plot 741) and for the other drug-treated groups (e.g., change from −48% to −44% in plot 743), which could thus indicate that the decrease in withdrawal latency response suffered by Group 2 was due to the ineffectiveness of the PLGA-amitriptyline alone as a pain treatment drug.

As shown in the plot 743 of FIG. 7, Group 3, which was treated with PLGA-clonidine, as mentioned above, demonstrated an increase in mean withdrawal latency response, as shown by the bar graphs, which are in contrast to the bar graph trends shown in plots 741 and 742 for Groups 1 and 2, respectively. As shown in the plot 743, the percent change for the mean withdrawal latency response improved from −62% post-surgery to −44% after 9 days of drug treatment, indicating an increase in pain tolerance and a gradual return to health. Bundled with the partial efficacy demonstrated in the plot 623 of FIG. 6, the plot 743 indicates that PLGA-clonidine may function as a partially effective pain treatment drug. Thus, those in Group 3 demonstrated a partial response to drug treatment, and thus a partial return to health.

As shown in the plots 744, 745, and 746, Groups 4, 5, and 6, respectively, which were treated with PLGA-carbamazepine, PLGA-lidocaine, and PLGA-celecoxib, respectively, demonstrated a significant increase in mean withdrawal latency response, as an example. As shown, referring to plot 744, the percent change for the mean withdrawal latency response of Group 4 improved from −58% post-surgery to 0% after 9 days of drug treatment, indicating a sharp increase in pain tolerance and a full return to health. Similarly, referring to plot 745, the percent change for the mean withdrawal latency response of Group 5 improved from −51% post-surgery to −22% after 9 days of drug treatment, indicating a significant increase in pain tolerance and a gradual return to health. A very similar trend can be seen in plot 746 for Group 6, as an example, which made a mean withdrawal latency response improvement from −58% up to −13%. As such, PLGA-carbamazepine, PLGA-lidocaine, and PLGA-celecoxib administered to Groups 4, 5, and 6, respectively, demonstrated efficacy according to their respective mean hot plate test results as compared to the control group shown in plot 741. Bundled with the efficacy demonstrated in plots 624, 625, and 626 in FIG. 6, the plots 744, 745, and 746, respectively, indicate that PLGA-carbamazepine, PLGA-lidocaine, and PLGA-celecoxib may be effective drug treatments.

As mentioned previously above, the body weights of the test rats were measured on three occasions at pre-operation prior to sciatic nerve constriction procedure, at time of test or control article dosing Day 0, and at termination at Day 10 post dose. Groups 1, 3, 4, 5 and 6, treated with diluent CMC solution (control), PLGA-clonidine, PLGA-carbamazepine, PLGA-lidocaine, and PLGA-celecoxib, respectively, continued to gain weight as expected over the study period, and remained normal per health and activity observations, indicating no likely adverse effect from their vehicle or drug treatments. Group 2, which was treated with PLGA-amitriptyline, demonstrated a decline in mean body weight with no other adverse health issues observed. Group 2's mean body weight loss coincided with the observed lack of efficacy (shown previously in FIG. 6, for example) and was in marked contrast to the weight gain observed for the control group and for the other drug treated groups (i.e., Groups 3-6), perhaps indicating that the weight loss of Group 2 was potentially related to the PLGA-amitriptyline drug treatment.

As described above, the outcomes of the Phase I study illustrated in FIG. 6 and FIG. 7 indicate that Groups 4 (PLGA-carbamazepine), 5 (PLGA-lidocaine) and 6 (PLGA-celecoxib) demonstrated a complete response to drug treatment, while Group 3 (PLGA-clonidine) demonstrated a partial response to drug treatment, according to both the hot plate test (FIG. 7) and the von Frey test (FIG. 6) endpoint methodologies. As mentioned above, none of the four drug-treated Groups 3, 4, 5, and 6 showed any adverse effects on weight gain or behavior according to their body weight endpoints. As such, one can conclude that the drugs administered to each of the test groups cause no adverse side effects, such as weight gain or behavioral changes, which were directly monitored during the study. Thus, an advantage of the disclosed method of treatment is that neuropathic pain can be effectively treated without the experience of significant adverse side effects.

As evidenced by the outcomes of the von Frey and hot plate tests, the five tested drugs administered at the previously-listed effective doses, at varying levels, functioned to treat diabetic neuropathy pain. In particular, Group 4, treated with PLGA-carbamazepine, Group 5, treated with PLGA-lidocaine, and Group 6, treated with PLGA-celecoxib each showed efficacy in the von Frey test and the hot plate test, as described above. Thus, as described previously in this disclosure, a comprehensive medicament set may be provided comprising the aforementioned drugs for use in clinical administration, such that to simultaneously regulate the pain receptors of the body. As will be demonstrated in the Phase II study below, the combination of two or more of the drugs increases the pain treatment found in the test subjects.

Phase II Study

As mentioned previously above, the rat efficacy test disclosed herein was conducted in two phases. Based on the Phase I study outcomes, the most singularly effective drugs were selected to be used in combined drug formulations, as an example. Per the experiment, two combination formulations were selected for further testing: combination formulation 1 (Group 2: PLGA-carbamazepine+PLGA-celecoxib), and combination formulation 2 (Group 3: PLGA-carbamazepine+PLGA-lidocaine+PLGA-celecoxib). The purpose the Phase II testing was essentially to observe whether the combined drugs of each combination formulation yielded an additive effect or a synergistic effect. For the test, three groups of 6 rats per group were separated, with two groups being treated with an effective amount of a designated pain management medication and one group treated with diluent CMC solution (the control), which are described as follows:

Group 1 was assigned to dosing with diluent CMC solution (control)

Group 2 was assigned to dosing with PLGA-carbamazepine (CBZ-30 kda) at 5 mg/kg+PLGA-celecoxib (CXB-30 kda) at 1.5 mg/kg Group 3 was assigned to dosing with PLGA-carbamazepine (CBZ-30 kda) at 5 mg/kg+PLGA-celecoxib (CXB-30 kda) at 1.5 mg/kg+PLGA-lidocaine (LDC-40 kda) at 10 mg/kg As in Phase I, each of the above-listed test groups were subject to a hot plate test, as previously described when referring to FIG. 7, on five occasions as follows: at pre-operation (prior to sciatic nerve constriction procedure), post-operation after creating chronic compression of sciatic nerve but prior to medication treatment, and three times post-operation on Day 1 post dosing, Day 5 post dosing, and Day 10 post dosing. Mean values and the standard error of the mean (SEM) values, and percent change from baseline, were calculated for each test group for each occasion. The test results for the three groups measured at these intervals can be found summarized in FIG. 8, which will be described in detail below.

Figure 8:
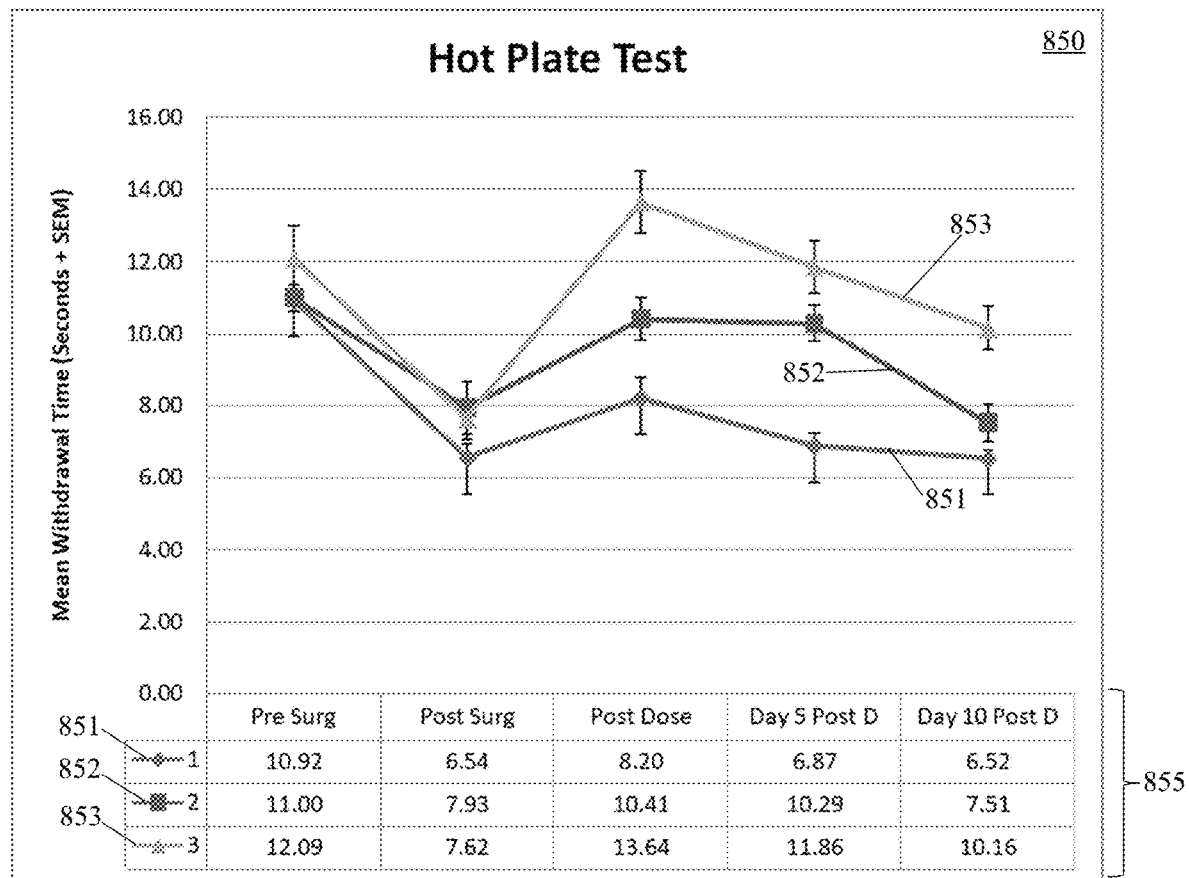
FIG. 8 is a plot illustrating the results of the hot plate test results conducted for the Phase II Study, according to an aspect.

FIG. 8 is a plot 850 illustrating the results of the hot plate test results conducted for the Phase II Study, according to an aspect. As mentioned previously above, three groups of test rats were treated (dosed) with a selected drug treatment, with Group 1 receiving the control treatment, Group 2 receiving the combination formulation 1, and Group 3 receiving the combination formulation 2, for example. As shown in FIG. 8, the plot 850 plots the mean withdrawal time, measured in seconds including the SEM, as indicated on the y-axis, of each test group against the occasions on which the hot plate tests were conducted, summarized in plot legend 820, as indicated on the x-axis. The mean withdrawal time, for example, was calculated based on the recorded time taken to observe a nociceptive response (e.g., hind paw lick, flinch, or jump) for each test group, as is known. The nociceptive response, for example, may thus serve as an indicator for the pain being experienced by a particular rat.

As shown in FIG. 8, the plot 850 illustrates the mean withdrawal time for Group 1, shown at 851, for Group 2, shown at 852, and for Group 3, shown at 853, as an example. The mean withdrawal time measured on each occasion (e.g., Pre Surg, Post Surg, etc.) can be found tabulated at 855, showing, on average, the time taken to observe a nociceptive response in each test group, for example. As mentioned above, Group 1 served as the reference control group, and received a dosing of diluent CMC solution, as an example. As shown at 851, and summarized in 855 for Group 1, on average, the time taken to observe a nociceptive response, in seconds, hovered between about 6.5 to over 8 seconds, after receiving the dose of diluent CMC solution. Referring now to curve 852, for Group 2, which received a dosing of the combination formulation 1 (PLGA-carbamazepine+PLGA-celecoxib), on average, the time taken to observe a nociceptive response hit a high of over 10 seconds post dose and 5 days after post dose (shown at 855), showcasing the ability of the drug combination formulation 1 to stay/prolong the rats' experiences of pain, for example. In comparison to the control Group 1, shown by curve 851, the combination formulation 1 improves well upon the control's pain treatment capabilities. Referring now to curve 853, for Group 3, which received a dosing of the combination formulation 2 (PLGA-carbamazepine+PLGA-lidocaine+PLGA-celecoxib), on average, the time taken to observe a nociceptive response hit a high of over 13 seconds post dose and almost 12 second 5 days after post does (shown at 855), showcasing the ability of the drug combination formulation 2 to significantly stay/prolong the rats' experiences of pain, as compared to that of the control Group 1.

As shown in FIG. 8 and described above, Groups 2 and 3 treated with combination formulation 1 and combination formulation 2, respectively, demonstrated efficacy according to their mean hot plate test results as compared to the control Group 1. Particularly, Group 3, which was treated with a combination of carbamazepine (anti-convulsant and sodium channel blocker), lidocaine (local anesthetic and sodium channel blocker) and celecoxib (COX-2 anti-inflammatory) showed the best efficacy between the two groups. Thus, as demonstrated by the hot plate tests conducted during Phase II of the study, the combination of a select number of the five drugs yielded a synergistic effect, especially for Group 3, for example, suggesting that the effect of the drugs in combination is greater than the sum of their respective separate effect (i.e., the drugs used individually, as tested during Phase I) at the same doses for treating neuropathic pain. Thus, an advantage of the disclosed method is that combinations of the disclosed drugs yield more effective medications, resulting in the increased effective treatment of neuropathic pain.

In conclusion, the combination of at least an anti-convulsant/sodium channel blocker, a local anesthetic/sodium channel blocker, and an anti-inflammatory drugs, as showcased in the hot plate test results of Group 3 in FIG. 8, was preferable for simultaneously regulating the pain receptors of the test rats, and thus for fully treating the pain associated with diabetic neuropathy effectively. As such, adding two more drugs, such as those administered during the Phase I study, to create a medicament set of five drugs may even more efficiently treat neuropathic pain, for example. Thus, the five above-described drugs may individually be combined to form a comprehensive medicament set adapted to regulate multiple receptors simultaneously in patients experiencing diabetic peripheral neuropathic pain, which are hereby supported by the rat studies.

It should be noted that all microsphere samples conducted in the example experiments described above were sterilized by gamma-irradiation at 25 kGy dosage. Before sterilization, each microsphere sample was weighed in a glass vial, purged with nitrogen gas for 10 minutes to prevent any oxidation from occurring, and sealed with an aluminum seal. It should also be noted that degradation of the encapsulated medication for each case was not observed during the sterilization process. It should also be noted that, per the experiments disclosed herein, 22G and 23G needles connected to a 1 cubic centimeter (cc) syringe were found to be optimal for injection of the microspheres by subcutaneous route due to the ease of withdrawal and lack of any clogging, for example.

Figure 9:
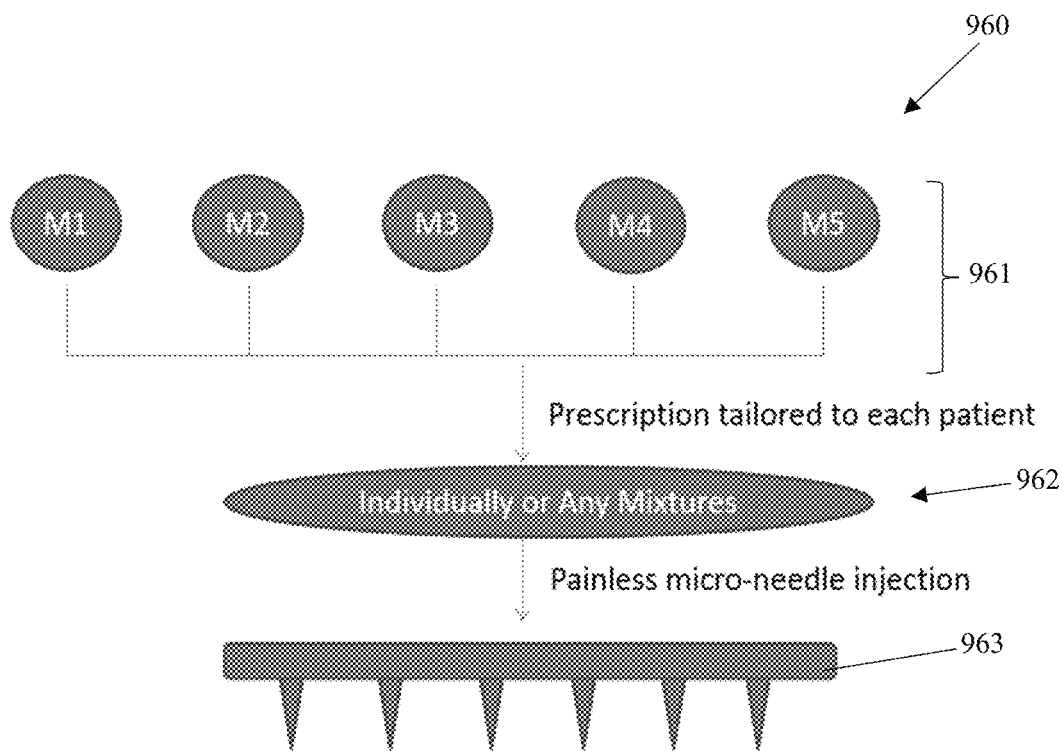
FIG. 9 is a diagram illustrating a method of administering a medicament set, according to an aspect.

FIG. 9 is a diagram illustrating a method 960 of administering a medicament set 961, according to an aspect. As described throughout this disclosure above, the medicament set 961 may be provided for the treatment of diabetic neuropathology pain, the medicament set 961 comprising a number of medicaments/medications (e.g., M1-M5), as shown in FIG. 9. As described previously above, each medication (i.e., M1, M2, M3 and so on) may be formulated as micro-particles having a size preferably between the critical range of 1 μm and 50 μm and being made of polylactic glycolic acid (PLGA) for the sustained and prolonged release over 2-8 weeks of a specific pain treatment drug (e.g., lidocaine, amitriptyline, celecoxib, etc.), for clinical administration as a locally injectable medicament using an injection device 963 (e.g., a painless microneedle or patch). From the medication set 961, any combination of medicaments can be made (e.g., M1+M2, M2+M4+M5, and so on), as indicated at 962 and as similarly discussed when referring to FIG. 8 above. A particular combination would be chosen and administered locally via the injection device 963 to a particular peripheral neuropathy patient based on particular information known by a medical care provider (e.g., a doctor) about the patient, particularly information about the receptors that need to be simultaneously regulated in that patient (after inspection and diagnosis, for example). Administration of the medicaments M1-M5 or any combination thereof by the doctor using the injection device 963 may thus cause a simultaneous regulation of the multiple receptor sites, such that to alleviate the pain being experienced by the patient having peripheral neuropathy, as an example. It should be understood that while five medicaments are shown in the medicament set 961 of FIG. 9, as many or as few medicaments as needed may be provided in a given medicament set for the treatment of a particular patient as deemed appropriate by a doctor administering the medicament set.

It should be understood that the tests and approaches conducted during the rat efficacy test are exemplary and other approaches may be taken to arrive at the same or similar conclusions. Additionally, it should be understood that the five selectively tested medications described throughout this disclosure above are representative of drugs falling within the same classification of drug, for example, and thus, the findings and outcomes concluded via the experiments herein may apply to those other non-explicitly tested drugs herein.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

Claim limitations should be construed as means-plus-function limitations only if the claim recites the term "means" in association with a recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples. Hence, the scope of the invention is defined by the accompanying claims and their equivalents. Further, each and every claim is incorporated as further disclosure into the specification.

What is claimed is:

1. A method of treating pain caused by diabetic peripheral neuropathy using a medicament set for regulation of multiple receptors simultaneously in a patient experiencing the pain, the method comprising the steps of:

receiving the medicament set, the medicament set comprising at least three distinct and separate medicaments for treating diabetic peripheral neuropathy pain, the three medicaments being:

a first medicament for treating peripheral neuropathy pain, being formulated for clinical administration as a locally injectable medicament using an injection device, and comprising polylactic glycolic acid (PLGA) micro-particles being loaded with a sodium channel blocker and local anesthetic drug, the sodium channel blocker and local anesthetic drug being lidocaine;

a second medicament for treating peripheral neuropathy pain, being formulated for clinical administration as a locally injectable medicament using an injection device, and comprising PLGA micro-particles being loaded with a sodium channel blocker and anti-convulsant drug, the sodium channel blocker and anti-convulsant drug being carbamazepine; and a third medicament for treating peripheral neuropathy pain, being formulated for clinical administration as a locally injectable medicament using an injection device, and comprising PLGA micro-particles being loaded with an anti-inflammatory drug, the anti-inflammatory drug being celecoxib;

wherein the PLGA micro-particles of the first, the second, and the third medicaments have a size between 1 μm and 50 μm;

selecting all or a portion of the medicament set for clinical administration to the patient according to particular information known about the patient, including information about the receptors that need to be simultaneously regulated in the patient to alleviate pain;

loading the selected all or portion of the medicament set into an injection device; and administering the selected all or portion of the medicament set to the patient by local injection using the injection device, the administering of the selected all or portion of the medicament set causing a simultaneous regulation of the multiple receptor sites, and thus resulting in at least a partial alleviation of the pain being experienced by the patient having diabetic peripheral neuropathy.

2. The method of claim 1, wherein the medicament set further comprises:

a fourth medicament for treating peripheral neuropathy pain, being formulated for clinical administration as a locally injectable medicament using an injection device, and comprising PLGA micro-particles being loaded with an α-2 adrenergic receptor agonist drug; and a fifth medicament for treating peripheral neuropathy pain, being formulated for clinical administration as a locally injectable medicament using an injection device, and comprising PLGA micro-particles being loaded with a NMDA receptor antagonist drug;

wherein the PLGA micro-particles of the fourth and the fifth medicaments have a size between 1 μm and 50 μm.

3. The method of claim 2, wherein the NMDA receptor antagonist drug is ketamine, and the α-2 adrenergic receptor agonist drug is clonidine.

4. The method of claim 1, wherein the PLGA micro-particles of the at least three medicaments are designed to have a controlled, sustained release of the drug over a period of 2-8 weeks.

* * * * *